United States Patent
Keren

(10) Patent No.: US 6,574,500 B2
(45) Date of Patent: Jun. 3, 2003

(54) IMAGING METHODS AND APPARATUS PARTICULARLY USEFUL FOR TWO AND THREE-DIMENSIONAL ANGIOGRAPHY

(75) Inventor: Hanan Keren, Kfar Saba (IL)

(73) Assignee: Medimag C.V.I. Ltd., Kfar Saba (IL)

(*) Notice: Subject to any disclaimer, the term of this patent is extended or adjusted under 35 U.S.C. 154(b) by 0 days.

(21) Appl. No.: 09/946,168

(22) Filed: Sep. 5, 2001

(65) Prior Publication Data

US 2003/0073892 A1 Apr. 17, 2003

(51) Int. Cl.[7] ............................................. A61B 6/00
(52) U.S. Cl. .................. 600/431; 600/420; 600/425; 378/51; 382/130
(58) Field of Search .................. 600/407, 420, 600/425, 431, 458; 378/51, 98.11; 382/130

(56) References Cited

U.S. PATENT DOCUMENTS

| | | | |
|---|---|---|---|
| 5,125,018 A | * 6/1992 | Asahina | 378/98.12 |
| 5,647,360 A | * 7/1997 | Bani-Hashemi et al. | 600/425 |
| 5,690,106 A | * 11/1997 | Bani-Hashemi et al. | 600/425 |
| 5,743,266 A | * 4/1998 | Levene et al. | 600/458 |
| 5,841,830 A | * 11/1998 | Barni et al. | 250/363.09 |

* cited by examiner

Primary Examiner—Marvin M. Leteef
Assistant Examiner—Barry Pass
(74) Attorney, Agent, or Firm—G.E. Ehrlich Ltd.

(57) ABSTRACT

A method and apparatus for imaging a body by exposing the body to radiation transmitted through the body via successive angular portions from a radiation source on one side of the body to a radiation detector in alignment with the radiation source on the opposite side of the body; the radiation detector including a two-dimensional matrix of detector elements producing electrical outputs corresponding to the magnitudes of the radiation received by each detector element; the radiation source producing a conical beam sufficiently large such that each exposure covers all the detector elements in the two-dimensional array after traversing the body. Also described are a method and apparatus for producing angiographical images having an enhanced contrast-to-noise ratio (CNR) by subtracting, from each contrast image produced after injecting a contrast material, a masking image produced before injecting the contrast material, starting with the masking image determined to have a minimum change over its immediately preceding masking image in the respective sequence.

22 Claims, 9 Drawing Sheets

ECG AND ACQUISITION TIMING DIAGRAM

IMAGING METHODS AND APPARATUS PARTICULARLY USEFUL FOR TWO AND THREE-DIMENSIONAL ANGIOGRAPHY

FIELD AND BACKGROUND OF THE INVENTION

The present invention relates to methods and apparatus for imaging three-dimensional objects. The invention is particularly useful in angiography for imaging a person's vascular system, and is therefore described below with respect to this application.

Electromagnetic radiation has long been used to produce images of internal structures of the human body for purposes of diagnosis or treatment of diseases. One technique which has gained widespread use since the 1970's is computerized tomography (CT), sometimes called computerized axialtomography (CAT), in which a narrow beam of X-rays is swept across an area of the body and is recorded by a radiation detector as a pattern of electrical impulses, while a computer is used to integrate the data for many such sweeps and to reconstruct a three-dimensional image of the examined volume. In the current CT systems, the radiation source is generally a fan-shaped beam, and the radiation detector includes a line of detector elements aligned with the fan-shaped beam so as to detect the level of the radiation after having traversed the object being examined. The body is exposed to the radiation at a plurality of different image planes (slices), and at a plurality of different angular positions for each image plane, while a large number of gray levels of radiation are sensed by each detector element. For example, a typical procedure may involve in the order of 256 slices, each at 128 different angular positions, with each detector element recording up to 128 gray levels. Many reconstruction algorithms are known for reconstructing the three-dimensional image from this data, but nevertheless, because of the vast amount of data needed, the reconstruction procedure is done off-line, rather than in real-time on-line.

Angiography, on the other hand, involves the radiographic examination of arteries and veins, in which a contrast medium is injected into the vascular system to cause a denser shadow than would be caused by other tissues, thereby enabling the blood vessels to be distinguished from the other tissues. In digital subtraction angiography (DSA), an X-ray image (called a; "masking image") of the patient is taken before the contrast material is injected; another X-ray image (called a "contrast image") is taken after the contrast material is injected; and the masking image is subtracted from the contrast image to leave only the DSA image of the blood vessels enabling them to be distinguished from the other tissue. Examples of known DSA systems are described in U.S. Pat. Nos. 5,630,414, 6,052,476, and 6,118,845, the disclosures of which are incorporated herein by reference.

At the present time, angiography is more widely used for producing a two-dimensional image, rather than a three-dimensional image, of the arteries and veins under examination. Making a three-dimensional examination using existing techniques would involve very costly equipment and/or substantial processing time so as to effectively preclude obtaining the results substantially at the time of the examination. As a result, it is necessary to search for the best angle for the two dimensional examination. This can be imprecise and somewhat awkward particularly since the examination involves the injection of the contrast material.

Providing angiographic images in three-dimensions, and in real-time with the performance of the diagnostic or treatment procedures, would substantially aid in reducing the dose levels and contrast media loads needed during the diagnostic or treatment procedure. Thus, providing the physician with three-dimensional angiographic views of the patient's vascular system in substantially real-time would enable the physician to analyze the three-dimensional angiography image directly, to decide on the best treatment strategy, and to determine the best projection angle for the treatment, such as the positioning of catheters, coils, balloons or stents.

In addition, the value of the images produced by DSA for diagnostic or treatment purposes depends to a high degree on the contrast-to-noise ratio (CNR) of the DSA image. The CNR of an image is to be distinguished from the signal-to-noise ratio (SNR), and is generally defined as being the difference in the SNRs of adjacent imaged regions. Thus, enhancing the CNR of a DSA image would better enable the physician to discern details of the patient's vascular system and therefore better enable the physician to utilize this information for diagnostic or treatment purposes.

OBJECTS AND BRIEF SUMMARY OF THE INVENTION

An object of the present invention is to provide a method and apparatus for producing a three-dimensional image of a body in real time. Another object of the invention is to provide a method and apparatus for producing three-dimensional angiographic images in real time to better enable diagnosis or treatment of a disease in the human body. A further object of the invention is to provide a method and apparatus for enhancing the CNR of a DSA image.

According to one aspect of the present invention, there is provided a method of imaging a body, comprising the steps: (a) exposing the body from one angular position with respect to the body, to radiation transmitted through the body from a radiation source on one side of the body to a radiation detector in alignment with the radiation source on the opposite side of the body; the radiation detector including a two-dimensional matrix of detector elements producing electrical outputs corresponding to the magnitudes of the radiation received by each detector element; the radiation source producing a conical beam sufficiently large to cover all the detector elements in the two-dimensional array after traversing the body; (b) successively changing the angular position in a plurality of angular increments over a predetermined angular sector, and repeating the exposing step at each of the angular positions; (c) storing the electrical outputs of each of the detector elements in each of the angular positions; and (d) utilizing the stored outputs for reconstructing and displaying the image of the body in three dimensions.

According to another aspect of the present invention, there is provided apparatus for imaging a body, comprising: a support for the body to be imaged; a radiation source at one side of the body to be imaged, the radiation source producing a conical beam to be transmitted through the body; a radiation detector at the opposite side of the body to be imaged and aligned with the radiation source; the radiation detector including a two-dimensional matrix of detector elements each producing an electrical output corresponding to the magnitude of the radiation received by the detector element; the conical beam produced by the radiation source being sufficiently large to cover all the detector elements in the two-dimensional array; a drive for effecting relative rotation, to a plurality of different angular positions, between the body on the one hand and the radiation source and radiation detector on the other hand, while keeping the radiation detector aligned with the radiation source; a computer for receiving the electrical outputs of each of the detector elements in each of the plurality of different angular positions, and for reconstructing the image of the body in three dimension; and a display for displaying the image of the body in three dimensions or in a selected plane.

According to further features in one described preferred embodiment, the electrical output of each detector element is digitized to binary values according to whether the magnitude of the radiation received by the respective detector element is above or below a predetermined threshold. Before the successive exposures, a contrast material is introduced into the body, which results in a first binary value (e.g., "0") being produced when the contrast material is not in the path of the radiation to the detector element, and a second binary value (e.g., "1") being produced when the contrast material is in the path of the radiation to the detector element.

According to one described preferred implementation, the stored outputs of the detector elements are utilized for reconstructing and displaying the image of the body in three dimensions by dividing the exposed volume into a three-dimensional array of voxels, and comparing the stored outputs of the detector elements for each of the voxels with look-up tables previously stored in the computer.

According to a second described preferred implementation, the stored outputs are utilized for reconstructing and storing the image of the body in three dimensions by dividing the exposed volume into a three-dimensional array of voxels, and utilizing the voxels in which the second value (e.g., "1") is present for all angular positions of exposure of the body for reconstructing and storing the image of the body in three dimensions. In this described implementation, the angular position of the radiation source and the radiation detector is changed in angular increments (of θ) around the longitudinal axis (e.g., the Z-axis) of the body being imaged. Also, for better resolution, the angular position of the radiation source and the radiation detector is also changed in angular increments (of β) around another axis (e.g., the X-axis) perpendicular to the longitudinal axis of the body being imaged.

Because in both of the above implementations of this described preferred embodiment, the apparatus includes a two-dimensional array of detector elements (rather than a line as in conventional CT apparatus), and because the apparatus needs to make only a few series of exposures at different angular positions (rather than a large number of such series of exposures or slices at different axial positions as in CT examination), and further, because the computer needs to distinguish between only two levels of data from each detector element (rather than many gray levels as in CT examination), this embodiment of the present invention can produce a three-dimensional image of the volume under examination in virtually real-time, as compared to existing techniques. For example, if exposures at 128 angular increments are made along only a few axes of the examined body, at a rate of 25 exposures per second, the exposure process would take only about 5 seconds per axis. Such a method and apparatus are therefore particularly useful in producing angiographs of a patient's vascular system in a virtually real-time manner and on-line with the diagnosis or treatment of the patient.

According to a still further aspect of the present invention, there is provided a method, and apparatus, for angiographically imagining a portion of a patient's vascular system to enhance the CNR of the produced image. Briefly, this is done by: producing a sequence of masking images of the portion of the patient's vascular system; determining the masking image in the sequence having a minimum change over its immediately preceding masking image in the sequence; injecting a contrast material into the patient's vascular system; producing a corresponding sequence of contrast images of the portion of the patient's vascular system while containing the contrast material; and subtracting from each contrast image of the sequence the corresponding masking image in the sequence starting with the minimum change masking image, to thereby produce a difference image having an enhanced contrast-to-noise ratio (CNR).

Further features and advantages of the invention will be apparent from the description below.

Such a method and apparatus can be used for both two-dimensional angiography as well as for three-dimensional angiography.

BRIEF DESCRIPTION OF THE DRAWINGS

The invention is herein described, by way of example only, with reference to the accompanying drawings, wherein.

DESCRIPTION OF PREFERRED EMBODIMENTS

The Embodiment of FIGS. 1–10

Figure 1:
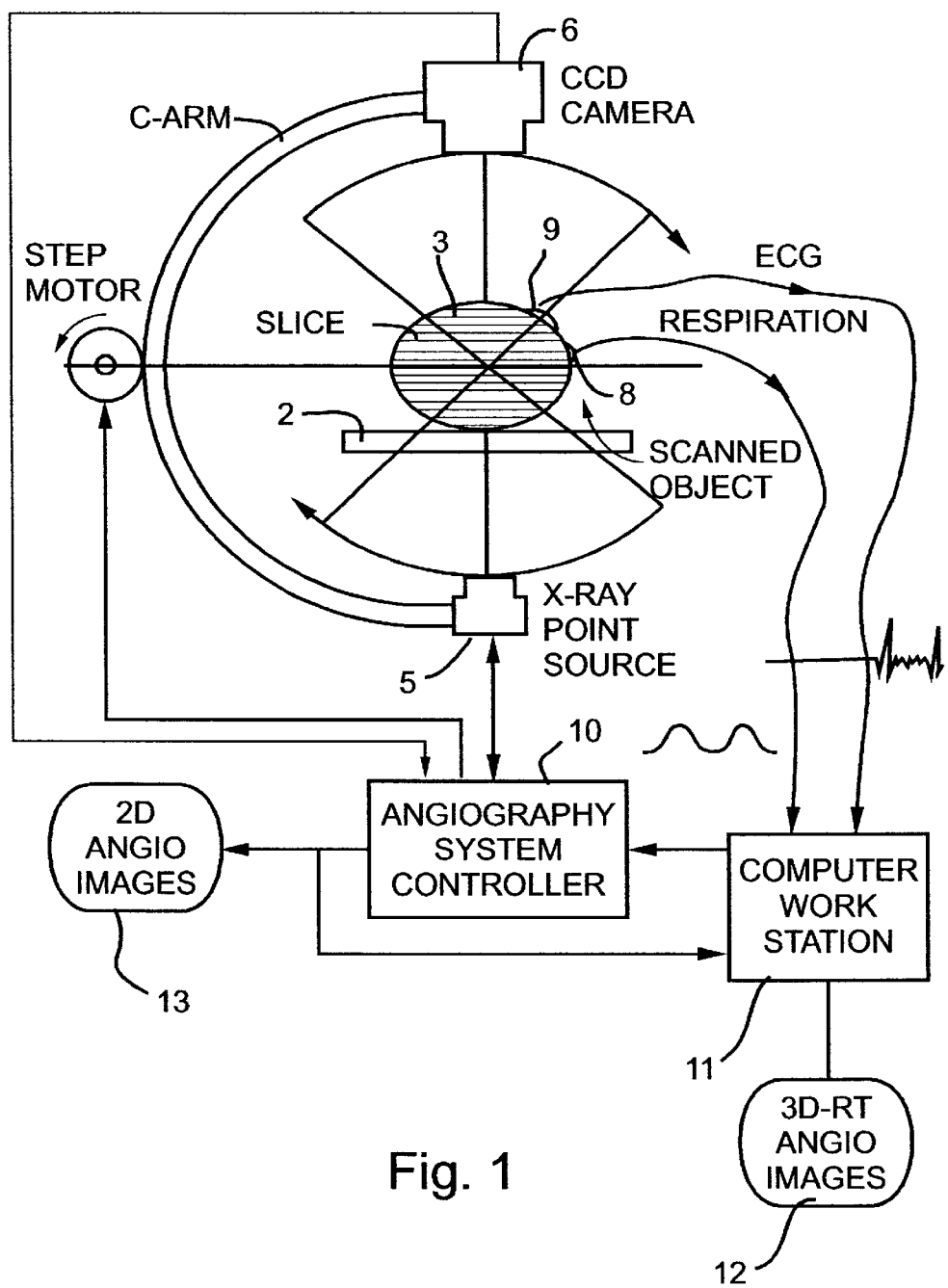
FIG. 1 is a diagram schematically illustrating one form of apparatus constructed according to the present invention.

FIG. 1 schematically illustrates one form of apparatus constructed in accordance with the present invention particularly useful for producing three-dimensional angiographs of a patient's vascular system.

Figure 2:
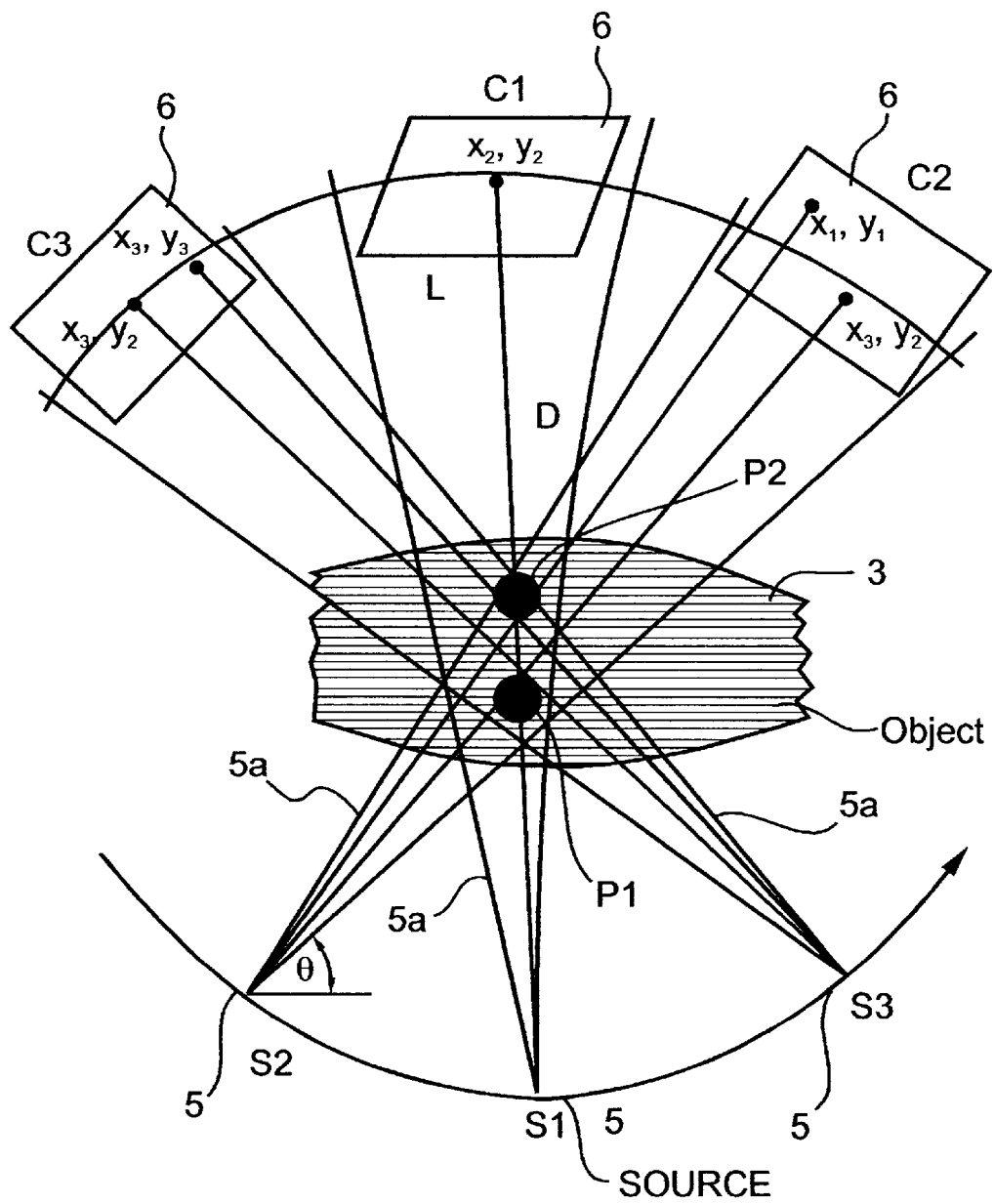
FIG. 2 more particularly illustrates how the apparatus of FIG. 1 is used for producing exposures at a plurality of different angular positions with respect to the body.
Figure 4:
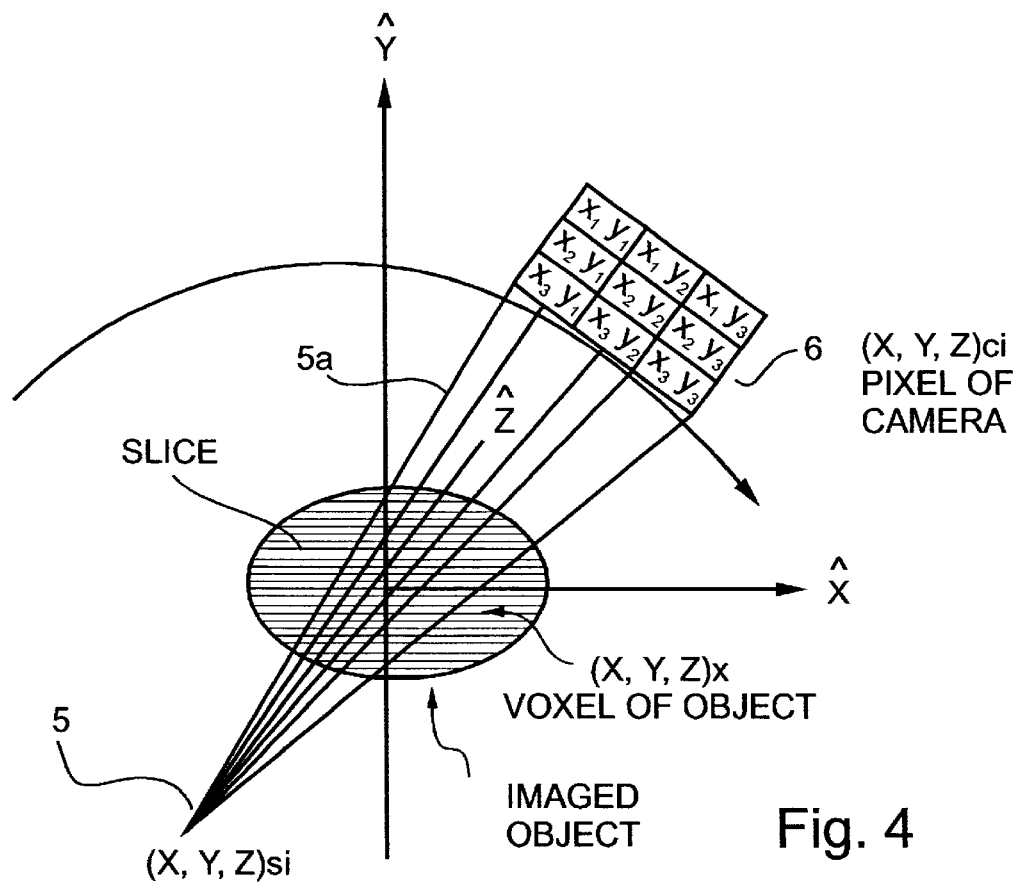
FIG. 4 is a diagram more particularly illustrating the two-dimensional matrix of detector elements in the radiation detector included in the apparatus of FIG. 1.

The system illustrated in FIG. 1 includes a horizontal support 2 for the patient 3 under examination, and a gantry C-arm 4, such as used in CT examination apparatus, straddling the patient's body 3. The C-arm supports a radiation source 5 at one side of the patient's body, and a radiation detector 6 at the opposite side and in alignment with the radiation source. The radiation source 5 is an X-ray point source which produces a conical beam 5a as shown in FIG. 2; and the radiation detector 6, preferably a CCD camera, includes a two-dimensional matrix of detector elements as best seen in FIG. 4. As shown particularly in FIG. 2, the conical beam 5a produced by the radiation source 5 in each angular position is sufficiently large to cover all the detector elements in the two-dimensional matrix 6 after traversing the body 3 under examination.

The apparatus illustrated in FIG. 1 further includes a step motor 7 for changing the angular position of the radiation source 5 and radiation detector 6 with respect to the body 3 under examination. In the preferred embodiment of the invention described below, the step motor 7 is capable of rotating the radiation source 5 and the radiation detector 6 about the Z-axis, which is the longitudinal axis of the patient's body 3, and also about the X-axis, which defines with the Z-axis the plane of the horizontal body support 2.

The apparatus illustrated in FIG. 1 may be used to acquire the examination data in synchronization with cardiac and/or respiratory gating. Accordingly, the illustrated apparatus includes a respiration sensor 8, and/or an ECG sensor 9, attached to the body 3 under examination.

The electronics in the apparatus illustrated in FIG. 1 includes an angiography system controller 10 which controls the radiation source 5 and also the step motor 7 to successively produce the exposures of the body 3 from a plurality of different angular positions with respect to the body. Controller 10 A also receives the electronic outputs from the radiation detector elements in the CCD camera 6, and processes those outputs as will be described more particularly below.

The apparatus illustrated in FIG. 1 further includes a computer work station 11 connected to the respiration sensor 8 and ECG sensor 9. Computer work station 11 controls the angiography system controller 10 in synchronization with the cardiac and/or respiratory gating produced by these sensors. The computer work station 11 is in turn controlled by controller 10 to produce a three-dimensional real-time display of the angio images on a monitor 12 at the work station. The illustrated system includes a further monitor 13 controlled by controller 10 to produce two-dimensional angio images of any selected plane in the volume under examination.

Figure 3:
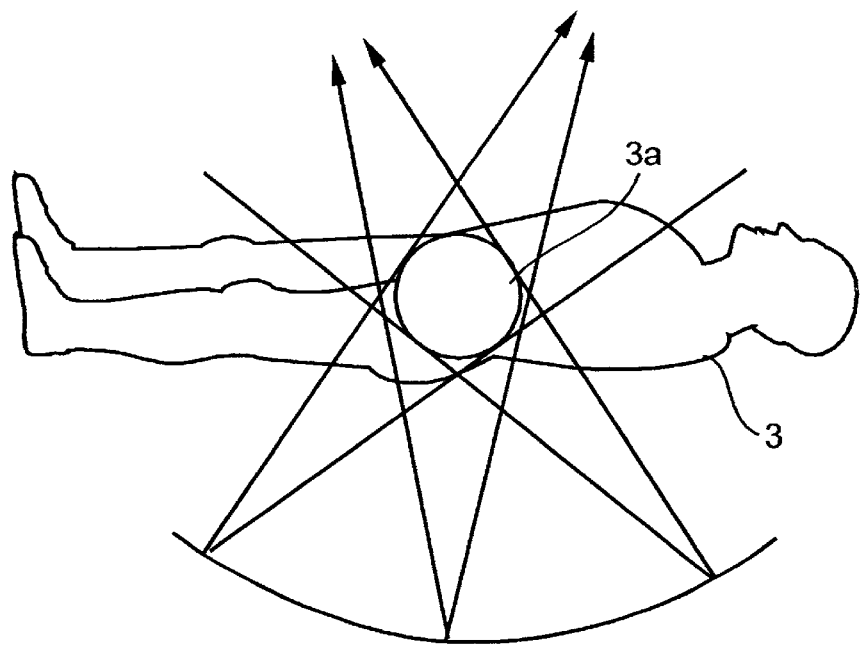
FIG. 3 is a diagram illustrating the volume examined by the plurality of exposures at the different angular positions.

FIG. 2 illustrates three angular positions ($S_1, S_2, S_3$) about the Z-axis of the radiation source 5 with respect to the body 3 under examination; while FIG. 3 schematically illustrates the volume 3a of the body 3 under examination in these three angular positions. FIG. 4 schematically illustrates the two-dimensional matrix of the detector elements in the radiation detector 6, and the radiation received thereby during the exposure at one angular position of the radiation source 5.

With reference to FIG. 2, points $S_1, S_2$ and $S_3$ denote three locations of the X-ray source 5 at three angles of θ; $C_1, C_2$ and $C_3$ denote the three locations of the camera 6 at these three angles; and $P_1$ and $P_2$ denote two different voxels (volume elements) within the examined volume 3a of the scanned object 3 at these three angular positions.

Figure 5:
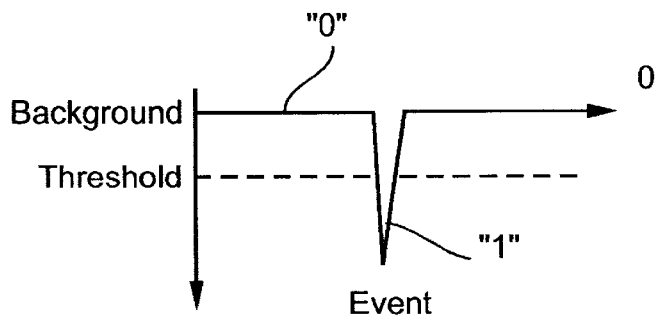
FIG. 5 is a diagram illustrating the threshold technique for digitizing the detector element outputs into binary form for reconstructing the three-dimensional image of the object being examined.

As indicated earlier, the output of each detector element of the camera 6 is digitized to produce only two binary values, depending on whether the detected radiation is above or below a predetermined. This is illustrated in FIG. 5. As also indicated earlier, before the exposures are made, a contrast material is introduced into the body 3, which contrast material results in the first value being produced in a detector element where the contrast material is not in the path of the radiation transmitted through the body to the detector element, and a second value being produced in a detector element where the contrast material is in the path of the radiation to the detector element. Thus, assuming the contrast material produces a "black" detector output where present, and a "white" detector output where not present, each detector element, based on the threshold illustrated in FIG. 5, will produce a "0" where background is detected, and a "1" where contrast material is detected.

FIG. 4 illustrates a simplified two-dimensional matrix of detector elements, showing only three horizontal rows (x) and three vertical columns (y). It will be appreciated that the CCD camera 6 would include a much larger number of detector elements, preferably a matrix of at least 128 by. 128 detector elements, and more preferably a matrix of 256 by 256 or 512 by 512 detector elements. In the simplified illustration of FIG. 4, the three horizontal rows of detector elements are identified as $X_1$–$X_3$; and the three vertical columns are identified as $Y_1$–$Y_3$.

In the example illustrated in FIG. 2, when the radiation source 5 is in the position $S_1$, it is aligned with both voxels $P_1$ and $P_2$. Accordingly, the radiation traveling from the source 5 received by the detector element in line $S_1$, $P_1$ and $P_2$ will be influenced by the condition of voxels $P_1$ and $P_2$; this detector element is $X_2, Y_2$, for example, in the matrix of the 6.

In this example, when the radiation source is in the position $S_2$, the condition of voxel $P_1$ will be indicated by detector element $X_3, Y_2$, and the condition of voxel $P_2$ will be indicated by detector element $X_1, Y_1$; and when the radiation source is in position $S_3$, the condition of voxel $P_1$ will be indicated by detector element $X_3, Y_2$, and the condition of voxel $P_2$ will be indicated by detector element $X_3, Y_3$. Thus, if these voxels contain a contrast material, indicating the presence of a blood vessel at this location, the respective detector elements will output an electrical signal which, when compared to the threshold illustrated in FIG. 5, will be a "1"; otherwise, the detector elements will output signals which, when compared to the threshold, will be "0".

Figure 6:
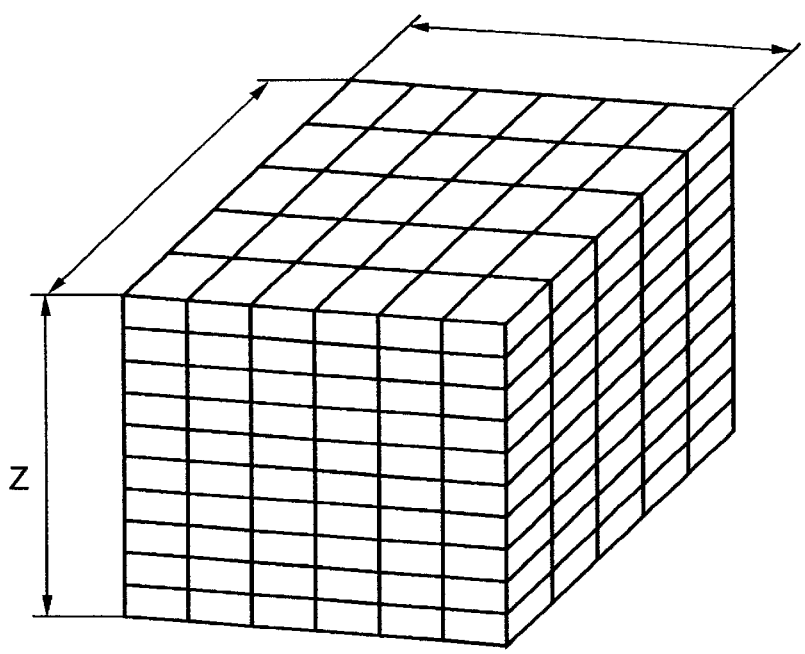
FIG. 6 is a diagram of the three-dimensional array of the imaged points (voxels) within the examined volume.

FIG. 6 illustrates how the cubical volume 3a (FIG. 3), which is examined by successively exposing the body 3 from a plurality of different angular positions, is divided into a three-dimensional array of voxels. With each angular exposure of the body 2, all the voxels in the respective plane or slice are examined.

An exposure of the body is first made while the two-dimensional array of detector elements 6 is parallel to the X-Z plane, whereby the voxels along the X-axis and Y-axis of the cubical volume 3a shown in FIG. 6 are examined; and then the body is exposed with the two-dimensional array of detector elements located in the Y-Z plane, whereby the voxels along the Y-axis (as well as the Z-axis) are examined. However, if only these two exposures were made, there would be considerable ambiguities since a voxel may show an element during one exposure caused by the shadowing of that voxel by another voxel in the same line during the respective exposure. To reduce or eliminate such ambiguities, the body is subjected to a number of exposures at different angular positions, as will be described more particularly below; and a determination is made that a particular voxel in the three-dimensional array shown in FIG. 6 is occupied by a detected element only when that voxel shows the presence of a detected element in all such exposures.

After all the exposures in the different angular positions have been completed, as will be described more particularly below the complete volume of voxels illustrated in FIG. 6 will have been divided into a three-dimensional array of voxels, each indicating by a "1" the detection of contrast material (and therefore a blood vessel point) therein, and by a "0" the absence of contrast material (and therefore no blood vessel point therein).

When all the exposures have thus been made in all the different angular positions, and the resultant data stored in a form representing the three-dimensional array illustrated in FIG. 6, the computer 10 utilizes this data to reconstructed the three-dimensional vascular system. This may be done by using previously recorded look-up tables, as shown by the flow chart in FIG. 8, or by using the algorithm shown in the flow chart of FIG. 9.

Figure 7:
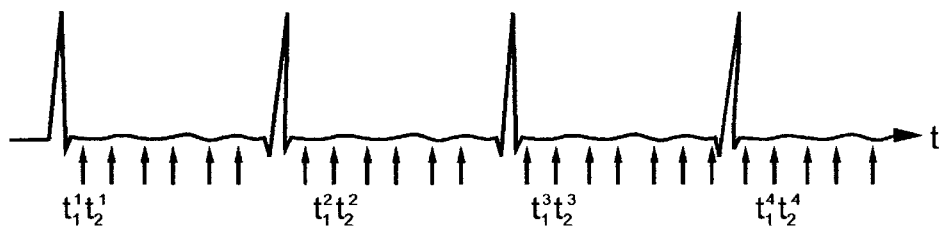
FIG. 7 illustrates a manner of acquiring the raw data in synchronization with cardiac and/or respiratory gating.

In either case, the exposures by the radiation source can be done in synchronization with the respiration or heart beats by using the signals from the respiration sensor 8 or the ECG sensor 9, for controlling the operation of the radiation source 5 and the computer 10. FIG. 7 illustrates an example of an ECG (or respiration) timing diagram for producing an image at every heart beat (or breath). Such synchronization is not necessary where stationary blood vessels are to be viewed.

Figure 8:
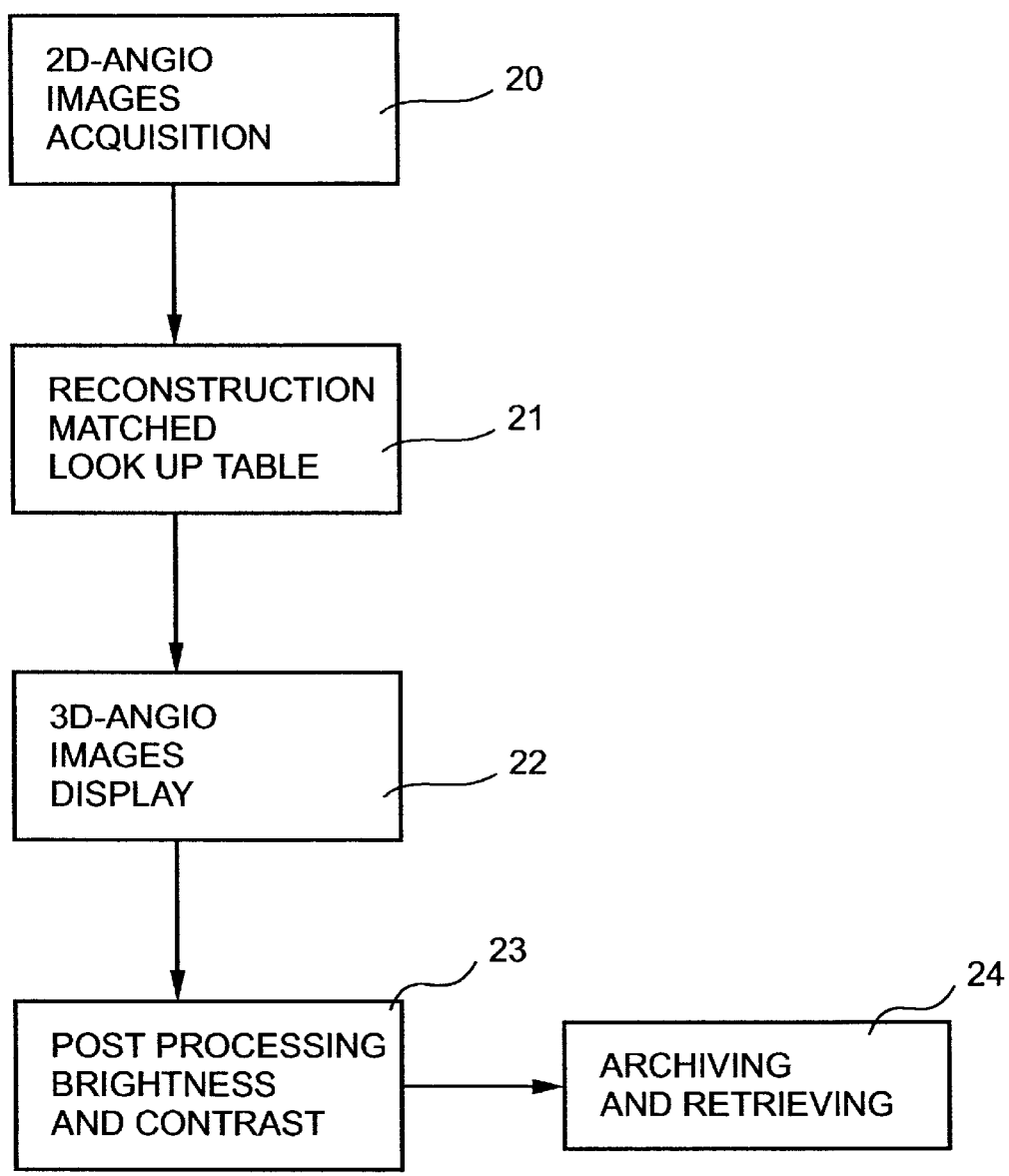
FIG. 8 is a flow chart illustrating one mode of operation of the computer in the apparatus of FIG. 1.

FIG. 8 is a flow chart illustrating one operation of the apparatus of FIG. 1 using previously-recorded look-up tables.

Thus, with reference to FIG. 1, the C-arm 4 is located in one angular position with respect to the body 3 to be examined such that the X-ray source 5 is below the body, and the CCD camera 6 is on the opposite side above the body with the two-dimensional array of detector being parallel to the X-Z plane. During this exposure, the X-ray point source 5 produces a conical beam which is sufficiently large to cover all the detector elements in the CCD camera 6 after traversing the body 3.

After such exposure, the C-arm 4 is rotated by the step motor 7 one angular increment (θ) about the Z-axis (the longitudinal axis of the body 3), and the body is again exposed to the radiation from the X-ray source 5 while the results are detected by the CCD camera 6. Such incremental exposures may be repeated at angular increments (θ) about the Z-axis over a predetermined angular sector of at least 90°. The electrical output of each of the detector elements in the CCD camera 6, in each such angular position, is stored in the controller 10.

However, the electrical output of each of the detector elements is first digitized to the binary values (0, 1), according to whether the magnitude of the radiation received by the respective detector element is above or below a predetermined threshold (FIG. 5). Also, before the exposure steps, a contrast material is introduced into the body under examination, such that a first value (e.g., "0") is produced in a detector element where the contrast material is not in the path of the radiation to the detector, and a second value (e.g., "1") is produced in the detector element when the contrast material is in the path of the radiation to the detector element.

It will be seen that when the exposure is made while the two-dimensional detector array is in the X-Z plane, the voxels of the cube in FIG. 6 along the X-axis and Z-axis will detect the presence or absence of contrast material in the respective voxels; and when the detector array is in the Y-Z plane, the voxels along the Y-axis will detect the presence or absence of contrast material in the respective voxels. However, if only these two planes are imaged, there will be considerable ambiguities since the presence of contrast material in a voxel will mask all the voxels in the same line of exposure, even though no contrast material may actually be in the respective voxel along a different line of exposure. For this reason, exposures are made in a number of additional planes, by rotating the two-dimensional detector array from the X-Z plane about the Z-axis, and preferably also about the X-axis.

The foregoing operations are represented by block 20 in the flow chart of FIG. 8. The three-dimensional reconstruction of the image of the examined body, i.e., the patient's vascular system identified by the contrast material, may be effected by previously-recorded look-up tables. These images may then be displayed (block 21), may be controlled with respect to brightness and contrast (block 23); and may be archived and retrieved (block 24). The operations indicated by blocks 21, 22, 23 and 24 can be implemented by existing commercially-available software.

Figure 9:
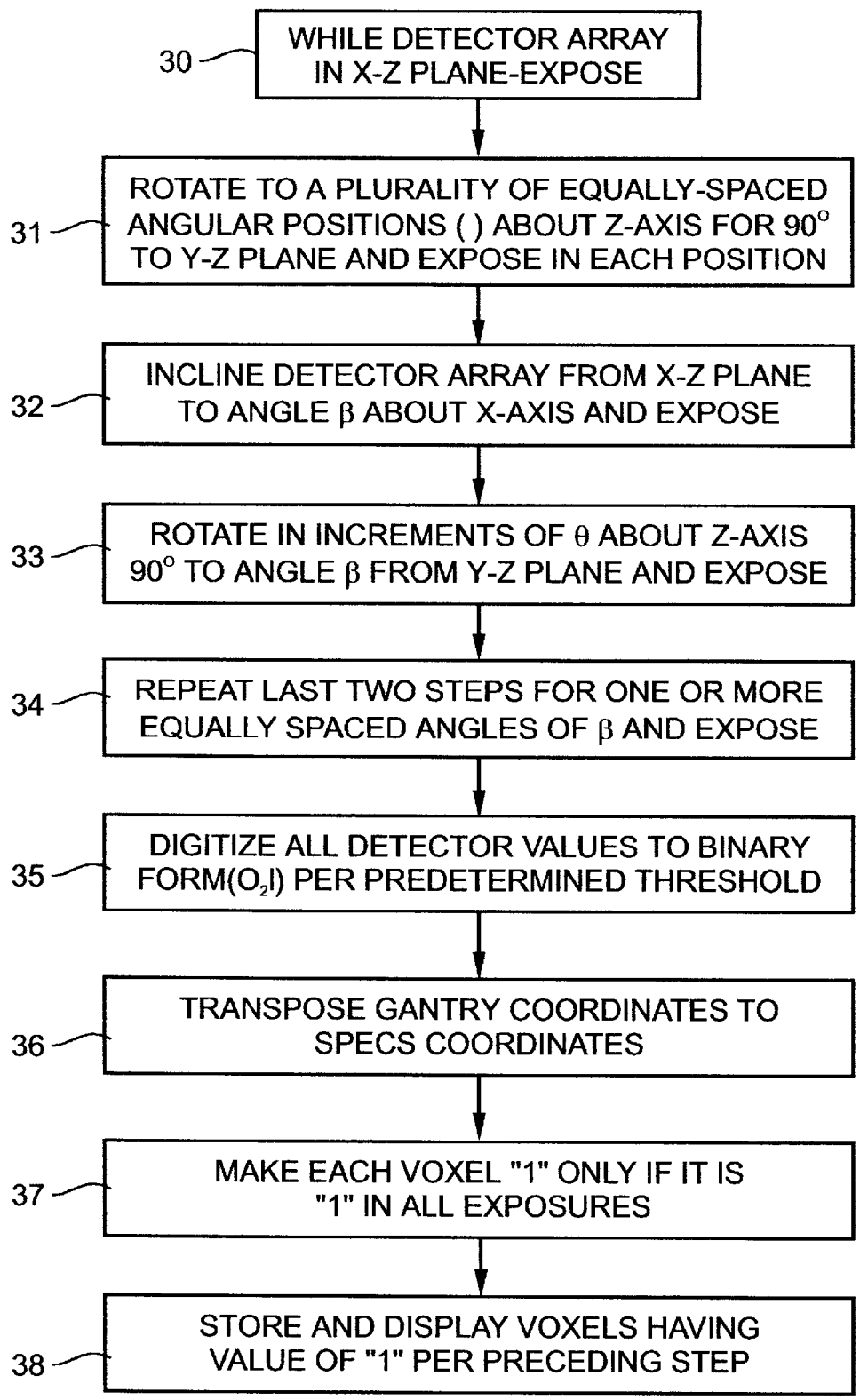
FIG. 9 is a flow chart illustrating another mode of operation of the computer in the apparatus of FIG. 1.

FIG. 9 is a flow chart illustrating another manner of implementing blocks 20 and 21 of FIG. 8.

Thus, as shown in FIG. 9, the detector array is first placed in the X-Z plane and an exposure is made (block 30). The two-dimensional detector array 6 is then rotated to a plurality of equally-spaced angular positions about the Z-axis for an angular distance of 90°, i.e., to the Z-plane, while an exposure is made in each such position (block 31). While the detector array is in the X-Z plane, it will detect contrast material in the voxels along the X-axis and Z-axis; and when the detector array is in the Y-Z plane, it will detect the presence of contrast material in the voxels along the Y-axis (as well as along the Z-axis). The detector array, however, is also exposed at a plurality of equally spaced angles (θ) during the rotation about the Z-axis, to enable the contents of the voxels within the three-dimensional array of FIG. 6 to be further examined to reduce or eliminate the ambiguities caused by contrast material in one voxel masking all the voxels in the same line of exposure, as described above.

The further exposures indicated by block 32 in FIG. 9 are provided in order to further reduce or eliminate such ambiguities. For this purpose, the detector array is inclined from the X-Z plane to the angle β about the X-axis and exposed (block 32); and then it is rotated in increments of θ about the Z-axis for an arc of 90° while at angle B from the Y-Z plane, and exposures of the detector array are made at all these portions (block 33). The steps of blocks 32 and 33 may be repeated for one or more equally-spaced angles of β, as indicated by block 34.

For example, there may be 22, or 64, or 128 equally spaced rotational θ positions in the above described procedures, and a similar number of equally-spaced β positions, according to the resolution desired.

The detector outputs in all the foregoing positions are digitized to binary forms (0, 1) according to a predetermined threshold, as described above (block 35).

As shown by block 36, the gantry coordinates are then transposed to base coordinates. The procedure described below may be used for this purpose.

Transform each object point (X, Y, Z) to (X', Y', Z') as obtained in the initial exposure steps, in the X-Z and Y-Z planes; according to its coordinates, transform inside the gantry frame of reference while scanning around Z-axis at the various angular rotational positions θ in two steps as follows:

(1) First, transform the points in the spatial coordinates (X, Y, Z), due to the inclination by angle β around the X-axis while the gantry is in up-down position (i.e., the normal to the detector array is vertical), to the gantry coordinates (X", Y", Z") according to following matrix form:

$$\begin{pmatrix} X'' \\ Y'' \\ Z'' \end{pmatrix} = \begin{pmatrix} 1 & 0 & 0 \\ 0 & \cos(\beta) & \sin(\beta) \\ 0 & -\sin(\beta) & \cos(\beta) \end{pmatrix} \begin{pmatrix} X \\ Y \\ Z \end{pmatrix}$$

(2) Second, transform the gantry coordinates (X", Y", Z"), due to the rotation by angle θ around the Z-axis after the gantry has been inclined by angle β around the X-axis, to the new gantry coordinates (X', Y', Z') as follows:

$$\begin{pmatrix} X' \\ Y' \\ Z' \end{pmatrix} = \begin{pmatrix} \cos(\theta) & \sin(\theta) & 0 \\ -\sin(\theta) & \cos(\theta) & 0 \\ 0 & 0 & 1 \end{pmatrix} \begin{pmatrix} X'' \\ Y'' \\ Z'' \end{pmatrix}$$

As described above, and as shown in block 37 of FIG. 9, each voxel in the three-dimensional array of voxels of FIG. 6 is considered as containing a detected element (contrast material) only of it contained the value "1" in all the exposures at all the rotational angles θ and β. Accordingly, the condition of the voxels in the three-dimensional array will indicate the three-dimensional configuration of the object to be detected in the body, namely the vascular system of the patient, and can be used for displaying such vascular system in three-dimensions or along any desired plane.

The larger the angular sector scanned during the examination process, the lower will be the error in the generated images. The examined volume is scanned over an angular sector of 90–180°, preferably 120°.

The number of angular increments of exposures within the scanning sector will determine the spatial resolution in the source-detector direction. Preferably, the detector 6 is at least 10 cm, more preferably at least 15 cm, in length along each side, and includes a matrix of at least 128 by 128, more preferably 256 by 256, or 512 by 512 detector elements. In the sample illustrated, the radiation detector 6 is at least 25 cm in length along each side, includes 512 by 512 detector elements in each plane (X-Y direction, FIG. 6), and 128 planes or slices (Z'direction, FIG. 6).

The exposures may be at the rate of about 25 frames per second. Accordingly, if there are 128 exposures around each axis, at the rate of 25 exposures per second the total exposure time would be slightly more than 5 seconds for each axis of rotation, such that the display would be virtually in real time as compared to previous techniques.

Figure 10:
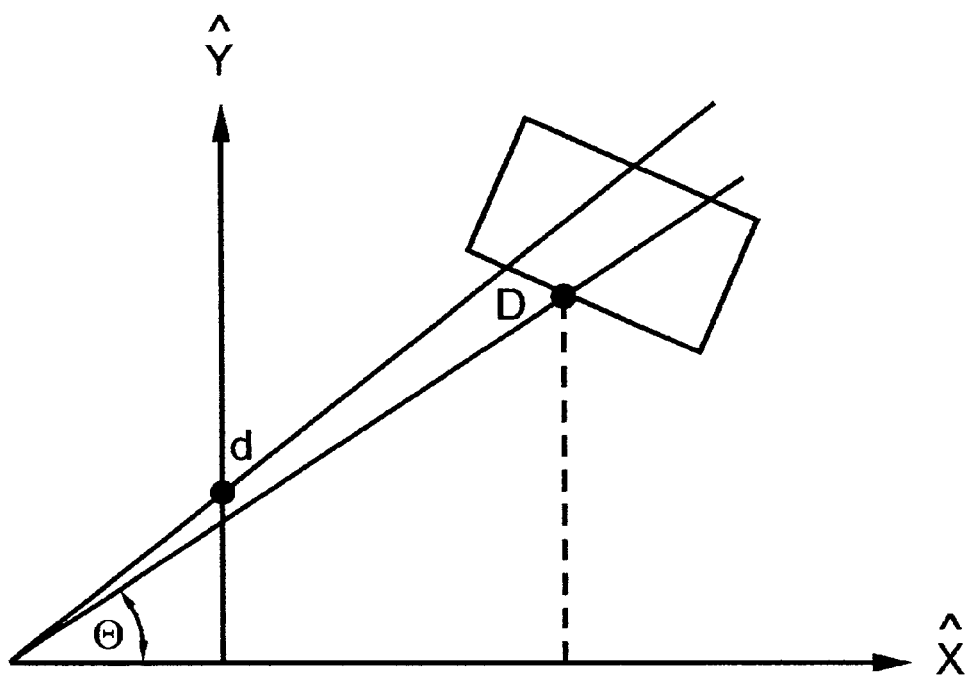
FIG. 10 is a diagram helpful in analyzing the error when using the apparatus and the method described herein.

FIG. 10 illustrates the manner of analyzing the error according to the angular increment (θ) between each exposure. Thus, with reference to the error analysis in FIG. 9:

D=(dcosθ).2 d=(D/2).1/cosθ

Ad=(d).(-Sinθ)

AD 2 cosθ

Reducing the angle θ towards 0°, and increasing the scanned sector reduces the error and improves the resolution.

Figure 11:
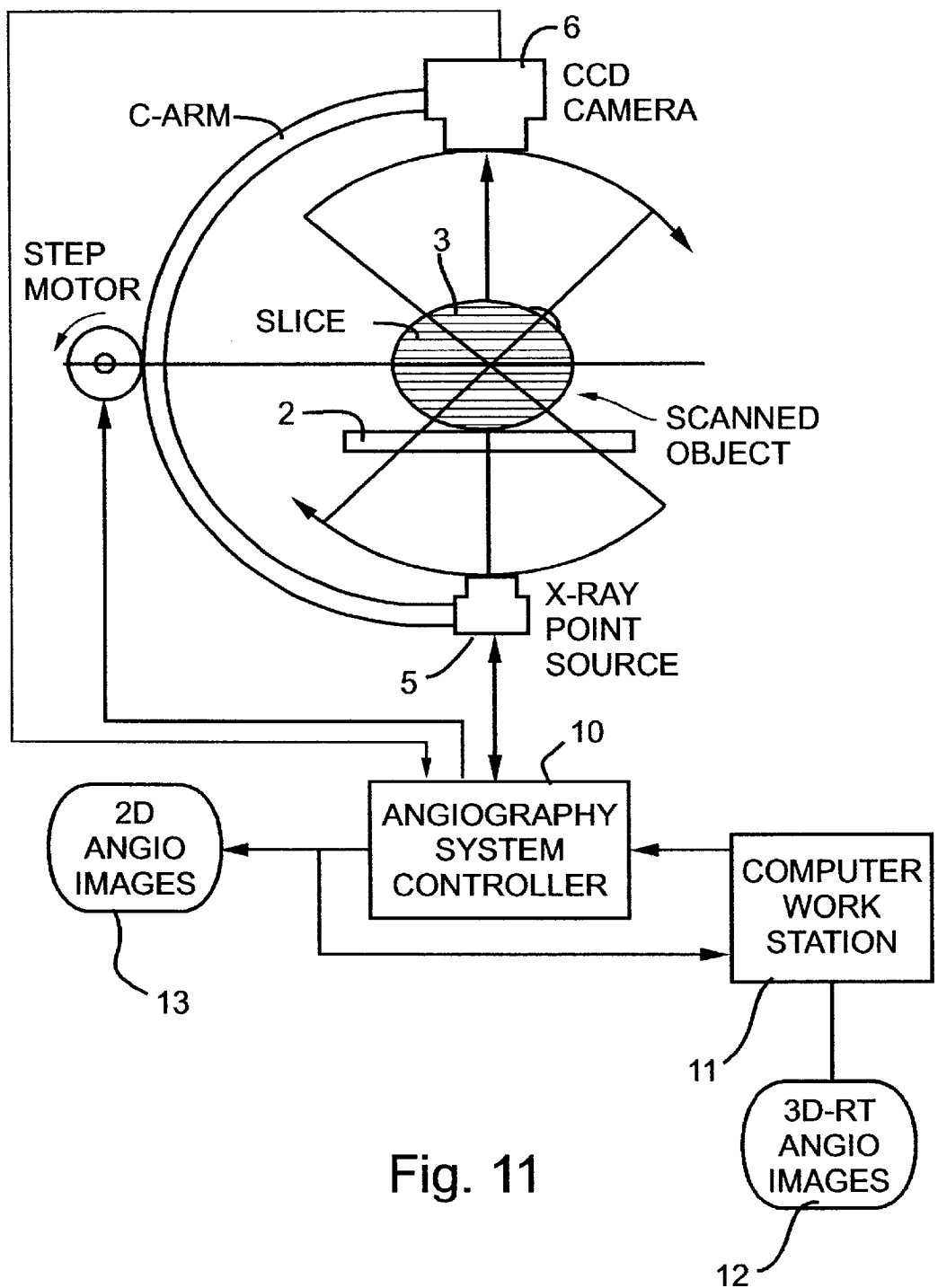
FIG. 11 is a diagram schematically illustrating another form of apparatus constructed in accordance with the present invention.
Figure 12:
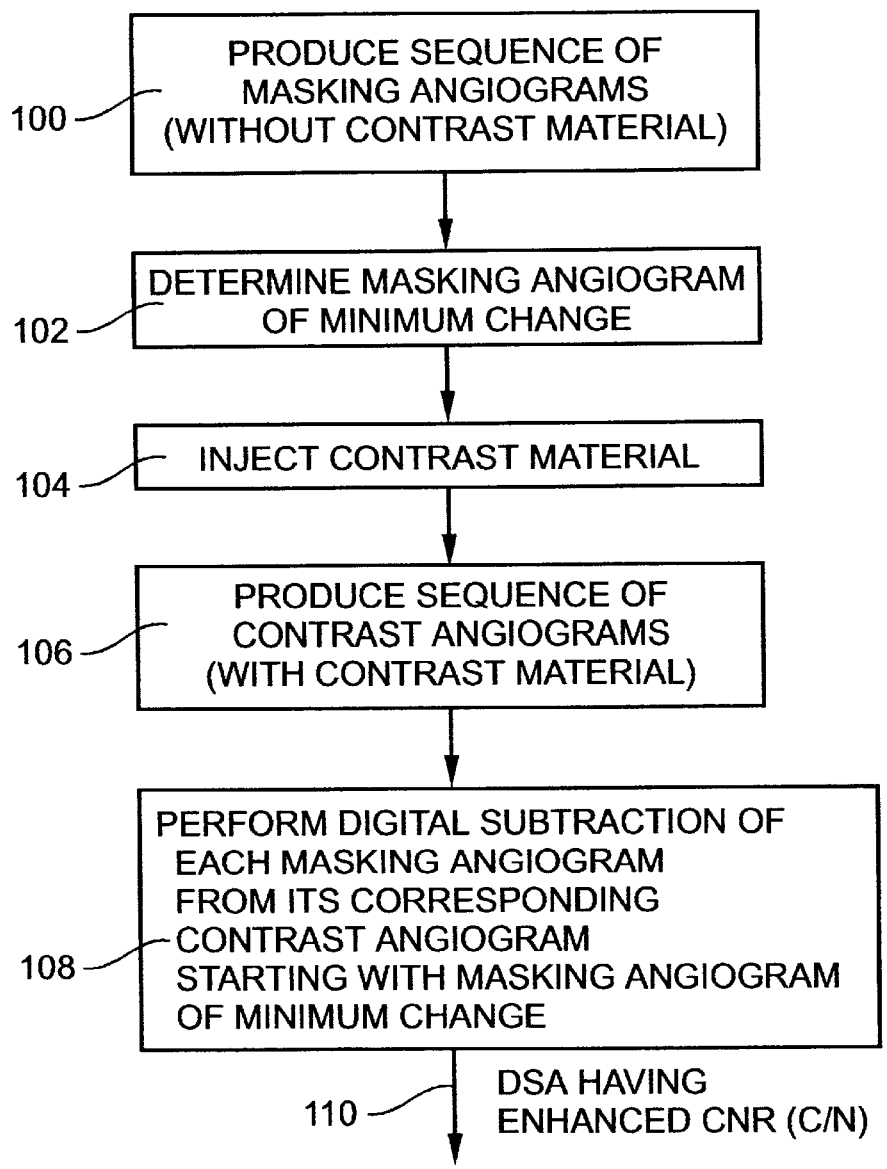
FIG. 12 is a flow chart illustrating the operation of the apparatus of FIG. 11.
Figure 13:
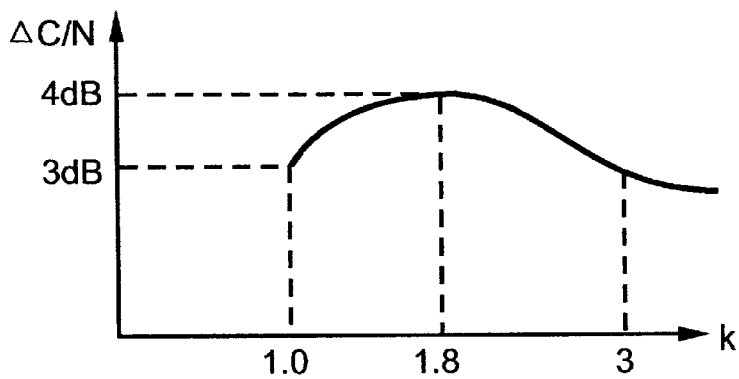
FIG. 13 is a diagram helpful in explaining the operation of the apparatus of FIGS. 11 and 12.

The Embodiment of FIGS. 11–13

FIG. 11 illustrates an apparatus similar to that of FIG. 1, except the respiration sensor 8 and the ECG sensor 9 are omitted, since the synchronization functions are performed in a different manner by the computer 11. The remainder of the system illustrated in FIG. 11 is substantially the same as described above with respect to FIG. 1, and therefore the same reference numerals have been used to identify corresponding parts to facilitate understanding.

As described above with respect to FIG. 1, the system illustrated in FIG. 11 may also be used for producing two-dimensional angio-images, as indicated by box 13, or three-dimensional angio-images as indicated by box 12.

FIG. 12 is a flow chart illustrating one manner of using the apparatus of FIG. 11 for producing DSA (digital subtracting angiograms) having an enhanced CNR (contrast-to-noise ratio) with respect to the portion of the patient's cardiovascular system examined by the apparatus.

Thus, as shown in the flow chart of FIG. 12, before a contrast material is injected into the patient, there is produced a sequence of masking angiograms (block 100); and a determination is made as to the masking angiogram having the minimum change over its immediately preceding angiogram (block 102). This may be done by comparing, on a pixel-by-pixel basis, the gray level of each pixel in the image with respect to the pixels in the immediately preceding masking image of the sequence, and determining which masking image has the minimum change over its immediately preceding masking image. For example, the sequence of masking images could be for a period of the order of 2–4 seconds, so that there would be about 50–100 images or frames in the respective sequence. The computer work station 11 stores all this information from each masking image in the sequence, and also makes the determination as to the masking image having the least change over its immediately preceding one.

The contrast material is then injected (block 104); and a corresponding sequence of contrast angiograms is now produced of the respective portion of the patient's vascular system, i.e., with the contrast material therein (block 106).

The computer then performs a digital subtraction of each masking image from its corresponding contrast image, starting with the masking image determined to have the least change over its immediately preceding masking image (block 108). The masking image determined to have the least change over its immediately preceding masking image is thus used as the reference point for this subtraction process, and thereby obviates the need for the ECG sensor 9 or the respiration sensor 8 illustrated in FIG. 1. It has been found that using the masking image of minimum change as a reference for the digital subtraction operation, produces a DSA having an enhanced CNR as compared to the previous techniques. Thus, using a respiration sensor 8 as the reference is not precise because of the difficulty in utilizing a particular point of the respiration curve for this purpose; and utilizing an ECG sensor is not precise for the same reason, but moreover, because the mere presence of the sensor can effect the ECG signal detected from the patient's body.

FIG. 13 is an emperical curve illustrating how the foregoing subtraction technique enhances the contrast-to-noise ratio (CNR). Thus, as shown in FIG. 13, if, in the subtraction step wherein the matching images are subtracted from their respective contrast images, the respective image is multiplied by a factor (k) of "1" there is an increase in the CNR of the resulting DSA of approximately 3 dB. That is, if the masking image is subtracted from the respective contrast image on a one-to-one basis, the enhancement of the CNR is approximately 3 dB.

FIG. 13, however, shows how this enhancement can be increased to about 4 dB, by changing the factor (k) to 1.8.

That is, if the masking image is subtracted from 1.8 times the respective contrast image, the enhancement of the resulting difference signal is increased about 4 dB.

As shown in FIG. 13, the factor (k) is therefore preferably from 1–3, to produce an enhancement of between 3 dB to 4 dB, in the particular example illustrated in FIG. 13.

It will be appreciated that, whereas FIG. 11 illustrates an apparatus for producing a three-dimensional angiogram, as well as a two-dimensional angiogram, the foregoing features of the invention could be used in a more simplified apparatus capable of producing only two-dimensional angiograms.

Also, while the invention has been described with respect to preferred embodiments, it will be appreciated that these are set forth merely for purposes of example, and that many other variations, modifications and applications of the invention may be made.

What is claimed is:

1. A method of imaging a body, comprising the steps:
   (a) exposing the body from one angular position with respect to the body, to radiation transmitted through the body from a radiation source on one side of the body to a radiation detector in alignment with the radiation source on the opposite side of the body; said radiation detector including a two-dimensional array of detector elements producing electrical outputs corresponding to magnitudes of the radiation received by each detector element; said radiation source producing a conical beam sufficiently large to cover all the detector elements in said two-dimensional array after traversing said body;
   (b) successively changing the angular position in a plurality of angular increments over a predetermined angular sector, and repeating said exposing step at each of said angular positions;
   (c) storing the electrical outputs of each of said detector elements in each of said angular positions;
   (d) and utilizing said stored outputs for reconstructing and storing an image of the body in three dimensions;
   said method further comprising the steps of injecting contrast material into the examined body; producing a masking image of the examined body before the injection of said contrast material; producing a contrast image of the examined body after injection of said contrast material; and producing a difference image by subtracting the masking image from the contrast image;
   said method further comprising enhancing the contrast-to-noise-ratio (CNR) of said difference image by the following steps—therefore;
   before an injection of contrast material, producing a sequence of said masking images, and determining the masking image in said sequence having a minimum change over its immediately preceding masking image in said sequence;
   and after injecting the contrast material, producing a corresponding sequence of said contrast images, and subtracting from each contrast image the corresponding masking image in the sequence starting with said minimum change masking image.

2. The method according to claim 1, wherein in step (d) the electrical output of each of said detector elements is digitized to binary values according to whether the magnitude of the radiation received by the respective detector element is above or below a predetermined threshold.

3. The method according to claim 2, wherein, before said exposing step (a), a contrast material is introduced into the body, which results in a first binary value being produced in a detector element where the contrast material is not in the path of the radiation to the detector, and a second binary value being produced in a detector element where the contrast material is in the path of the radiation to the detector.

4. The method according to claim 3, wherein said stored outputs are utilized for reconstructing and storing the image of the body in three dimensions by dividing an exposed volume of the body into a three-dimensional array of voxels, and utilizing the voxels in which said second binary value is present for all angular positions of exposure of said body for reconstructing and storing the image of the body in three dimensions.

5. The method according to claim 4, wherein, during said exposures, said body is located in space defined by the three orthogonal axes, X, Y, Z, wherein the Z-axis is the longitudinal axis of the body, and the X-axis defines with the Z-axis the plane of orientation of the body; and wherein said exposures of the body include exposures while the two-dimensional array of detector elements is:
   (a) in the X-Z plane;
   (b) in the X-Z plane; and
   (c) in a plurality of equally-spaced angular planes ($\theta$) rotated about the Z-axis.

6. The method according to claim 5, wherein said exposures further include exposures while the two-dimensional array of detector elements is:
   (d) in at least one further plane rotated to an angular position $\beta$ about the X-axis; and
   (e) in a plurality of such planes at equally-spaced angular positions ($\theta$) rotated about the Z-axis.

7. The method according to claim 6, wherein said exposures (d) and (e) are effected for a plurality of equally-spaced angular positions $\beta$ about the X-axis.

8. The method according to claim 1, wherein in step (b), the angular position of said radiation source and said radiation detector is changed in angular increments around a longitudinal axis of the body being imaged.

9. The method according to claim 8, wherein in step (b) the angular position of said radiation source and said radiation detector is also changed in angular increments around another axis perpendicular to said longitudinal axis of the body being imaged.

10. The method according to claim 1, wherein said stored outputs are utilized for reconstructing and storing the image of the body in three dimensions by dividing an exposed volume of the body into a three-dimensional array of voxels, and by comparing the stored outputs of the detector elements for each of said voxels with look-up tables previously stored in a computer.

11. The method according to claim 1, wherein the body is a patient, and said contrast material is injected into the vascular system of the patient to enable viewing an examined portion of said system in three dimensions, or in any selected plane.

12. The method according to claim 11, wherein the detector is selected such that it includes a matrix of at least 128 by 128 detector elements, and is at least 10 cm in length along each side.

13. The method according to claim 11, wherein the body is successively exposed in at least 128 angular increments over an angular sector of at least 90° around the longitudinal axis of the body being imaged.

14. The method according to claim 11, wherein said radiation source is selected such that it is a source of X-rays, and said radiation detector is selected such that it is an X-ray detector.

15. The method according to claim 1, wherein in said subtraction step, pixel-brightness values in the respective contrast image are multiplied by a factor (k) of 1 to 3 before the corresponding masking image is subtracted therefrom.

16. The method according to claim 15, wherein said factor (k) is 1.8.

17. A method of angiographically imaging a portion of a patient's vascular system, comprising:

produducing a sequence of masking images of said portion of the patient's vascular system;

determining the masking image in said sequence having a minimum change over its immediately preceding masking image in said sequence;

injecting a contrast material into the patient's vascular system;

producing a corresponding sequence of contrast images of said portion of the patient's vascular system while containing said contrast material;

and subtracting from each contrast image of said sequence the corresponding masking image in the sequence starting with said minimum change masking image, to thereby produce a difference image having an enhanced contrast-to-noise ratio (CNR).

18. The method according to claim 17, wherein in said subtraction step, pixel-brightness values in the respective contrast image are multiplied by a factor (k) of 1 to 3 before the pixel-brightness values in the corresponding masking image are subtracted therefrom.

19. The method according to claim 18, wherein said factor (k) is 1.8.

20. Apparatus for producing angiographical images of a portion of a patient's vascular system, comprising:

a radiation source to be located at one side of the patient for radiating said portion of the patient's vascular system;

a radiation detector to be located at the opposite side of the patient for producing electrical outputs corresponding to the magnitude of the radiation received by the detector;

a computer for controlling said radiation source and for processing the outputs of said radiation detector to produce an image of said portion of the patient's vascular system;

and a display for displaying said produced image;

said computer controlling said radiation source and processing the outputs of said radiation detector such that:

before a contrast material is injected into the patient's vascular system and a sequence of masking images is produced of the portion of the patient's vascular system, a determination is made as to the masking image in said sequence having a minimum change over its immediately preceding masking image;

and after a contrast material is injected into the patient's vascular system and a corresponding sequence of contrast images is produced, from each contrast image the corresponding masking image in the sequence is subtracted starting with the masking image determined to have a minimum change over its immediately preceding masking image, to thereby produce a difference image having an enhanced contrast-to-noise ratio (CNR) which is displayed in said display.

21. The apparatus according to claim 20, wherein said computer, before subtracting from each contrast image the corresponding masking image in the sequence, multiplies the pixel-brightness values of the respective contrast image by a factor (k) of 1 to 3 before the pixel-brightness values of the corresponding masking image are subtracted therefrom.

22. The apparatus according to claim 21, wherein said factor (k) is 1.8.

* * * * *